United States Patent [19]

Szantay et al.

[11] 4,425,358
[45] Jan. 10, 1984

[54] 13-THIA-PROSTACYCLINE DERIVATIVES

[75] Inventors: Csaba Szantay; Lajos Novák, both of Budapest; József Aszódi, Göd-felső; Vilmos Simonidesz, Budapest; Géza Galambos, Budapest; Gábor Kovács, Budapest; Sándor Virag, Budapest; István Stadler, Budapest; Péter Kórmóczy, Budapest, all of Hungary

[73] Assignee: Chinoin Gyogyszer es Vegyeszeti Termekek Gyara R.T., Budapest, Hungary

[21] Appl. No.: 370,503

[22] Filed: Apr. 21, 1982

[30] Foreign Application Priority Data

Apr. 22, 1981 [HU] Hungary .................................. 1035

[51] Int. Cl.³ .................. A61K 31/557; C07D 307/935
[52] U.S. Cl. .................................... 424/285; 549/454; 549/465
[58] Field of Search ................. 549/454, 465; 424/285

[56] References Cited

U.S. PATENT DOCUMENTS 4,232,009 11/1980 Hayashi et al. ..................... 424/285

Primary Examiner—Henry R. Jiles
Assistant Examiner—Bernard Dentz
Attorney, Agent, or Firm—Karl F. Ross; Herbert Dubno

[57] ABSTRACT

The invention relates to new optically active or racemic 13-thia-prostacycline derivatives of the Formula I

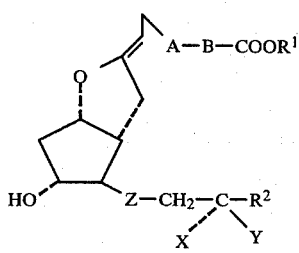

wherein
$R^1$ is hydrogen, a pharmaceutically acceptable cation or a straight or branched chain alkyl group having 1–5 carbon atoms;
$R^2$ is straight or branched chain alkyl having 4–9 carbon atoms or monosubstituted phenoxymethyl;
—A—B— is —$CH_2$—$CH_2$—, —CH=CH— of Z— or E— configuration or —C≡C—;
one of the symbols X and Y is hydrogen, methyl or ethyl and the other is hydroxy, tetrahydropyranyoxy, 1-ethoxy-ethoxy or trialkylsilyloxy; or
X and Y together form a —O—$CH_2$—$CH_2$—O— group;
Z is a sulfur atom or a —SO— group.

The compounds of the Formula I can be prepared by reacting a 13-thia-prostaglandine of the Formula III

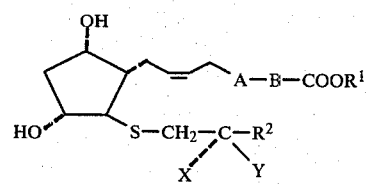

if desired after oxidation into the corresponding 13-oxide derivative—with a halogenating agent; and treating the 5-halogeno-13-thia-prostacycline of the Formula II

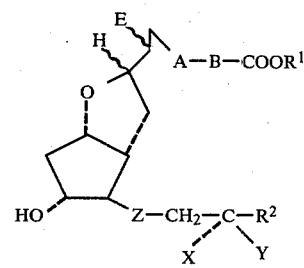

thus obtained wherein E is halogen with an organic or inorganic base; and thereafter if desired removing the protecting groups X and/or Y and if desired converting a compound of the Formula I obtained into a salt or setting free the same from a salt. The new compounds of the Formula I possess anti-coagulant and hypotensive properties and can be used in therapy.

11 Claims, No Drawings

13-THIA-PROSTACYCLINE DERIVATIVES

This invention relates to optically active or racemic new 13-thia-prostacycline derivatives, a process for the preparation thereof and pharmaceutical compositions containing the same.

According to an aspect of the present invention there are provided new optically active and racemic 13-thia-prostacycline derivatives of the Formula I

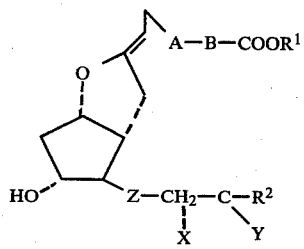

wherein $R^1$ is hydrogen, a pharmaceutically acceptable cation or a straight or branched chain alkyl group having 1-5 carbon atoms $R^2$ is straight or branched chain alkyl having 4-9 carbon atoms or monosubstituted phenoxymethyl;

—A—B— is —$CH_2$—$CH_2$—, —CH=CH— of Z- or E-configuration or —C≡C—;

one of the symbols X and Y is hydrogen, methyl or ethyl and the other is hydroxy, tetrahydropyranyloxy, 1-ethoxy-ethoxy or trialkylsilyloxy; or X and Y together form a —O—$CH_2$—$CH_2$—O— group Z is a sulfuratom or a —SO— group.

The new compounds of the Formula I can be regarded as the stabilized analogs of the biologically extremely active prostacycline. The said prostacycline had been first described in 1976 (S. Moncade et al: Nature 263, 663) and soon thereafter its chemical structure was clarified. [R. A. Johason et al: Prostaglandins 12, 915 (1976)]. Prostacycline is an intermediate of the metabolism of arachidonic acid and exhibits extremely strong und useful pharmaceutical effects already when administered in very low doses. From these effects the blood platelet aggregation inhibitory and vasodilatory activities seem to be the most promising because the said effects might enable the use of prostacycline in the treatment of prophylaxis of the nowadays highly widespread cardiovascular diseases—such as arteriosclerosis and thrombosis. A large number of articles dealing with the clinical use of prostacycline have been published (e.g. J. R. Vane and S. Bergström: Prostacycline, Raven Press, New York 1979).

The greatest difficulty to the practical use of prostacycline is its extreme instability.

Although the point of the prostacycline molecule most sensitive to chemical effects is the enolether structural unit ($C_{5-9}$)—in the presence of an external or internal proton source the molecule quickly decomposes to 6-oxo-$PGF_{2\alpha}$—its metabolism is unusually rapid. In the organism prostacycline is quickly inactivated by the prostaglandine dehydrogenase enzyme system under the oxidation of the $C_{13-20}$ structural unit. The free acid form of prostacycline is not stable; in pharmacological and clinical tests it is used in the form of a salt or an ester.

Prostacycline may be stabilized by carrying out a structural modification in the molecule which decreases the effect of the prostaglandine dehydrogenase enzyme system.

The new compounds of the Formula I comprise a sulfur atom and a methylene group or a —SO— group and a methylene group in place of the carbon-carbon double bond in positions 13,14 of the prostacycline molecule. Since the dehydrogenase enzyme system attacks at the positions 15 and 13-14, as a result of this modification the molecule can serve as a substrate for the prostacycline dehydrogenase enzyme system to a smaller extent while at the same time the valuable pharmacological effects of prostacycline remain preserved.

On plasma isolated from human blood and enriched in blood platelets the new compounds of the Formula I inhibit aggregation induced by $1 \times 10^{-6}$ mole/ml of ADP in a concentration of 50-100 mg/ml ($ID_{50}$; measured by the method of Born) which corresponds to a 1/10-1/50 of the effect of $PGI_2$.

On plasma isolated from rabbit blood and enriched in blood platelets the 50% inhibition of the aggregation induced by $1 \times 10^{-4}$ mole/ml of ADP can be achieved by using the esters of the compounds of the Formula I in a concentration of 1-10 μg/ml and the salts in a concentration of 500-900 ng/ml.

The effect of the compounds of the Formula I exerted on the blood pressure of pentobarbitural narcotized spontaneously breathing cats is about 1/100 of that of $PGI_2$ i.e. it is by two orders of magnitude lower that that of the prostacycline of natural origin.

Thus both the inhibition of aggregation and the blood pressure decreasing effect show a relationship between dose and effect.

On guinea pig trachea the compounds of the Formula I show a contracting effect similarly to $PGI_2$. The effect is, however, by approximately one order of magnitude weaker than that of $PGI_2$.

According to a further feature of the present invention there is provided a process for the preparation of racemic or optically active compounds of the Formula I which comprises reacting a 13-thia-prostaglandine derivative of the Formula III

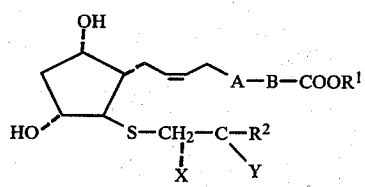

(wherein $R^1$, $R^2$, —A—B—, X and Y are as stated above)—if desired after oxidation into the corresponding 13-oxide derivative—with a halogenating agent; treating the 5-halogeno-13-thia-prostacycline derivative of the Formula II

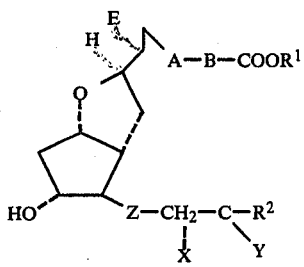

II.

thus obtained (wherein R¹, R², —A—B—, X,Y and Z are as stated above and E is halogen)—if E is bromine after separation of the endo isomer and if E stands for iodine in the form of the isomer mixture—with an organic or inorganic base; and thereafter if desired removing the protecting groups X and/or Y and if desired converting a compound of the Formula I obtained into a salt or setting free the same from a salt.

The reaction is carried out with a halogenating agent. As halogenating agent preferably iodine may be used. The reaction is carried out in the presence of a not too strong base, e.g. preferably potassium carbonate or sodium hydrogen carbonate. The reaction temperature is preferably about 0°–30° C. As reaction medium organic solvents—preferably dichloro methane or chloroform—may be used. The crude product isolated from the reaction mixture by extraction is subjected to purification by means of chromatographic methods.

When iodine is used as halogenating agent the product obtained contains more than 95% of the exo isomer (IIa)

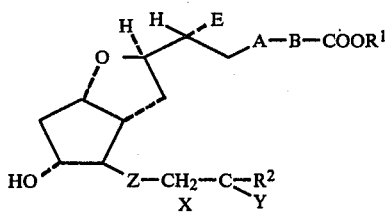

IIa.

and about 4% of the endo isomer (IIb)

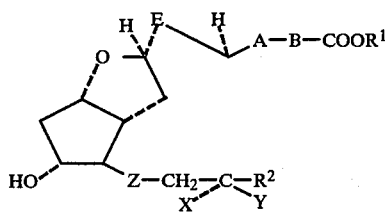

IIb.

so that it is not necessary to separate the two isomers.

When bromine is used as halogenating agent the endo isomer (IIb) is formed in a larger amount of about 10% so that it is separated from the exo isomer (IIa) and the separated exo isomer is used in the further reaction to form the desired endproduct of the Formula I.

The starting materials of the Formula III are partly known from Belgian Pat. No. 828925. The 13-thia-prostaglandine-13-oxide derivatives of the Formula III not disclosed therein (in which Z is —SO—) can be prepared from the corresponding known 13-thia-prostaglandine derivatives (Z is sulfur) by treatment with a mild oxidizing agent (preferably sodium periodate) in an aqueous-alcoholic medium preferably in a mixture of water and ethanol.

The compounds of the Formula II are treated with an organic or inorganic base in order to split off a hydrogen halide. For this purpose preferably 1,5-diazabicyclo[4.3.0]-non-5-en may be used. The reaction may be carried out in an anhydrous aprotic solvent (e.g. toluene) or an alcohol or in the absence of a solvent. The reaction temperature is between 25°–150° C., preferably 100°–120° C.

The compound of the Formula I can be isolated from the reaction mixture by washing, drying and evaporating the solvent. The endproduct thus obtained is generally of such purity that no further purification is required. If, however, a purification takes place, this can be carried out by column chromatography—with the exception of the free acids.

The term "pharmaceutically acceptable cation" used throughout the specification relates to mono-, di- or trivalent positive charges which do not cause any undesired side-effects when used in a dose corresponding to the compounds of the Formula I. The said cations may be preferably those of alkali metals (e.g. sodium, potassium or lithium), alkaline earth metals (e.g. calcium or magnesium), aluminum, ammonium ion or mono- or bivalent ammonium ions derived from organic amines [e.g. tris-(hydroxy-methyl)-ammonium ion].

The term "straight or branched chain alkyl group having 1–5 carbon atoms" covers the methyl, ethyl, n-propyl, isopropyl, n-, iso-, secondary and tertiary butyl and all the isomeric amyl groups.

The term "straight or branched chain alkyl group having 4–9 carbon atoms" covers all the isomeric butyl, amyl, hexyl, heptyl, octyl and nonyl groups.

The phenyloxymethyl group may bear one halogeno or trifluoromethyl substituent in any position of the phenyl ring.

The three alkyl substituents of the trialkylsylyl group may be the same or different and may be preferably alkyl groups having 1–5 carbon atoms defined above.

The term "organic base" relates to linear, branched or cyclic alkyl amines having one or more nitrogen atoms. Preferably the organic bases are the 1,5-diazabicyclo[4.3.0]non-5-en and triethyl amine.

The inorganic bases may be derived from alkali or alkaline earth metals. The said bases may be alcoholates, hydroxides, carbonates and hydrogen carbonates.

The alcohols used in the process of the present invention may be preferably alkanols having 1–5 carbon atoms.

As aprotic solvent preferably aromatic hydrocarbons (e.g. benzene, toluene) or halogenated hydrocarbons (e.g. chloroform, dichloromethane etc) may be used.

As halogenating agent preferably elementary halogens (e.g. iodine or bromine) may be used but other generally known halogenating agents may be used as well) e.g. N-bromo-succinimide or interhalogens).

According to the present invention there are also provided pharmaceutical compositions comprising as active ingredient at least one compound of the Formula I in admixture with suitable inert non-toxic carriers.

The pharmaceutical compositions according to the present invention may be prepared by methods of pharmaceutical industry known per se.

Further details of the present invention may be found in the following Examples without limiting the scope of protection to the said examples.

EXAMPLE 1

Preparation of 13-thia-13,14-dihydro-PGI$_2$-methylester (A) Preparation of 5-iodo-13-thia-13,14-dihydro-PGI$_1$-methylester To a solution of 102 mg (0.314 millimole) 13-thia-13,14-dihydro-PGF$_{2\alpha}$-methylester and 6 ml of anhydrous dichloromethane 118 mg (0.44 millimole) of twice sublimed iodine and thereafter a solution of 130 mg (0.94 millimole) of potassium carbonate and 20 ml of water is added under stirring. The reaction mixture is stirred at room temperature for 15–20 hours whereupon sodium thiosulfate is added until the color of iodine disappears. The organic phase is separated, the aqueous phase extracted with 5 ml of dichloromethane, the united organic phases are dried over magnesium sulfate and the solvent is distilled off. The residual oil is purified by column chromatography (Kieselgel G; a 7:3 chloroform-acetone mixture). Thus 105 mg of the named compound are obtained, yield 65%. According to chromatography the product contains more than 95% of the exo isomer (IIa) and 4% of the endo isomer (IIb).

$R_{F(exo)}=0.79$; $R_{F(endo)}=0.90$.

IR(NaCl): 3400, 1720, 1460, 1360, 1220, 1160, 1050 cm$^{-1}$.

$^1$H—NMR(CDCl$_3$): o=0.89 (3H, m), 1.3 (6H, m), 3.68 (3H, s), 4.0 (4H, mc.), 4.6 (2H, m).

Ms: M+ 514 (<1%), m/e 496 (2, M-18), 369 (3, M-18-I), 255 (22), 223 (54), 205 (6), 191 (18), 173 (7), 148 (21), 143 (20), 111 (37), 108 (59), 91 (14), 81 (71), 54 (100).

(B) Preparation of 13-thia-13,14-dihydro-PGI$_2$-methylester

To a solution of 142 mg (0.276 millimole) of 5-iodo-13-thia-13,14-dihydro-PGI$_1$-methylester and 20 ml of anhydrous toluene 0.172 g (1.38 millimole) of anhydrous 1,5-diazabicyclo[4.3.0]non-5-en is added under argon. The reaction mixture is heated to boiling for half an hour, then cooled and washed twice with a 2% potassium carbonate solution, dried over magnesium sulfate. The solvent is distilled off in vacuo. Thus 106 mg of the pure, compound named above are obtained, yield 99.5%.

$R_F=0.87$ (on a Kieselgel plate treated with triethylamine; a 7:3 chloroform-acetone mixture containing solid potassium carbonate).

IR(NaCl): 3350, 1730, 1635, 1440, 1360, 1220, 1150, 1110 cm$^{-1}$.

$^1$H—NMR(CHCl$_3$-piridin-D$_5$): δ 0,84 (3H, m), 1,3 (6H, m), 3,58 (3H, s), 4,6 (2H, mc).

Ms: M+ 386 (8%), m/e 368 (13, M-18), 355 (7), 239 (22), 221 (44), 196 (45), 143 (63), 121 (13), 111 (72), 83 (24), 79 (38), 55 (100).

EXAMPLE 2

Preparation of 15-epi-13-thia-13,14-dihydro-PGI$_2$-methyl ester (A) 15-epi-5-iodo-13-thia-13,14-dihydro-PGI$_1$-methyl ester To a solution of 159 mg (0.409 mg millimole) 15-epi-13-thia-13,14-dihydro-PGF$_{2\alpha}$-methyl ester and 12 ml dichloromethane a saturated aqueous solution of 340 mg (4.1 millimole) of sodium hydrogen carbonate is added, whereupon a solution of 114 mg (0.45 millimole) of twice sublimed iodine in 3 ml of dichloro methane is added at 0° C. with strong stirring. The reaction mixture is stirred at 0° C. for 8 hours and at room temperature for 10 hours whereupon sodium thiosulfate is added until the color of iodine disappears. The organic phase is separated, the aqueous layer extracted with methylene chloride and the united organic solutions are dried over magnesium sulfate. The solvent is distilled off in vacuo and the residue is purified by column chromatography. (Kiesel G; a 7:3 chloroform-acetone mixture).

Thus 124 mg of the title compound are obtained, yield 59%. According to chromatographical analysis the product contains more than 95% of the exo isomer (IIa) and 4% of the endo isomer (IIb).

$R_{F(exo)}=0.67$; $R_{F(endo)}=0.78$.

IR(NaCl): 3400, 1720, 1460, 1360, 1220, 1160, 1050 cm$^{-1}$.

Ms: M+ 514 (<1%), m/e 496 (1, M-18), 369 (4, M-18-I), 255 (20), 223 (58), 205 (7), 191 (17), 173 (7), 148 (21), 143 (22), 111 (38), 108 (60), 91 (14), 81 (71), 54 (100), 45 (60).

(B) Preparation of 15-epi-13-thia-13,14-dihydro-PGI$_2$-methylester

To a solution of 94 mg (0.18 millimole) of 15-epi-5-iodo-13-thia-13,14-dihydro-PGI$_1$-methyl ester and 10 ml of anhydrous toluene 0.112 g (0.9 millimole) of anhydrous 1,5-diazabicyclo[4.3.0]non-5-en is added under nitrogen. The reaction mixture is heated to boiling for an hour under stirring whereupon washed twice with a 2% aqueous potassium carbonate solution, dried over magnesium sulfate and the solvent is distilled off in vacuo. Thus 68 mg of the pure compound named above are obtained, yield 98%.

$R_F=0.82$ (on a Kieselgel plate treated with triethyl amine; a 7:3 mixture of chloroform and acetone containing solid potassium carbonate).

IR(NaCl): 3350, 1720, 1635, 1440, 1360, 1220, 1150 cm$^{-1}$.

$^1$H—NMR(CDCl$_3$-pyridin D$_5$): δ 0,86 (3H, m), 1,3 (6H, m), 3,62 (3H, s), 4,6 (2H, mc).

Ms: M+ 386 (7), m/e 368 (13, M-18), 355 (6), 239 (21), 221 (35), 196 (28), 195 (12), 143 (43), 138 (12), 137 (10), 131 (12), 121 (29), 115 (15), 111 (50), 109 (14), 97 (16), 95 (22), 83 (21), 81 (20), 79 (33), 67 (19), 59 (18), 55 (100), 43 (25), 41 (53).

EXAMPLE 3

Preparation of 13-thia-13,14-dihydro-15-dehydro-PGI$_2$-methyl-ester-ethylene ketal (A) Preparation of 5-iodo-13-thia-13,14-dihydro-15-dehydro-PGI$_1$-methylester-ethylene ketal To a solution of 147 mg (0.341 millimole) of 13-thia-13,14-dihydro-15-dehydro-PGF$_{2\alpha}$-methylester-ethylene-ketal and 7 ml of dichloromethane a solution of 140 mg of potassium carbonate and 1 ml of water is added whereupon a solution of 112 mg (0.443 millimole) of twice sublimed iodine and 2 ml of dichloromethane is added dropwise. The reaction mixture is stirred at room temperature for 15 hours, whereupon a saturated aqueous sodium thiosulfate solution is added dropwise until the color of iodine disappears. The organic layer is separated, the aqueous phase extracted with dichloromethane and the united organic layers are dried over magnesium sulfate. The solvent is distilled off in vacuo and the residual oil is purified by column chromatography. (Kieselgel G; a 7:3 mixture of chloroform and acetone).

Thus 120 mg of the named compound are obtained, yield 64%. According to chromatography the product contains more than 95% of the exo isomer (IIa).

$R_{F(exo)}=0.86$; $R_{F(endo)}=0.92$

IR(NaCl): 3370, 1720, 1440, 1410, 1360, 1220, 1180, 1160, 1110, 1060, 1040 cm$^{-1}$.

$^1$H—NMR(CDCl$_3$): $\delta$ 0,9 (3H, m), 1,3 (6H, m), 3,68 (3H, s), 4,0 (5H, mc), 4,6 (2H, mc).

Ms: M$^+$ 556 (<1%), m/e 497 (2), 496 (8), 495 (23), 494 (100), 463 (4), 438 (4), 386 (7), 368 (7), 254 (8), 223 (11), 209 (8), 189 (8), 144 (4), 143 (35), 127 (7), 115 (10), 111 (38), 99 (36), 91 (13), 81 (28), 79 (34), 71 (27), 55 (40), 44 (51).

(B) Preparation of
13-thia-13,14-dihydro-15-dehydro-PGI$_2$-methylester-ethylene ketal To a solution of 77 mg (0.136 millimole) of 5-iodo-13-thia-13,14-dihydro-15-dehydro-PGI$_1$-methylester-ethylene ketal and 10 ml of anhydrous toluene 0.084 g (0.679 millimole) of anhydrous 1,5-diazabicyclo[4.3.0]non-5-en is added under argon and the reaction mixture is heated to boiling under argon for more than an hour. The mixture is cooled to room temperature, washed twice with a 2% potassium carbonate solution and dried over magnesium sulfate. The solvent is distilled off in vacuo. Thus 58 mg of the named compound are obtained, yield 98%.

$R_F$=(9.94 on a Kieselgel plate treated with triethyl amine; a 7:3 mixture of chloroform and acetone, containing solid potassium carbonate).

IR(NaCl): 3350, 1720, 1635, 1440, 1360, 1220, 1150, 1110, 1030 cm$^{-1}$.

$^1$H—NRM(CDCl$_3$-pyridine D$_5$): $\delta$ 0,86 (3H, m), 1,26 (6H, m), 3,63 (3H, s), 4,1 (4H, mc), 4,6 (2H, m).

Ms: M$^+$ 428 (<1%), m/e 397 (1), 386 (3), 385 (7), 384 (26), 366 (5), 353 (8), 285 (6), 271 (18), 270 (20), 253 (17), 252 (8), 239 (21), 238 (9), 237 (8), 222 (6), 221 (22), 209 (7), 199 (15), 196 (30), 195 (18), 189 (12), 167 (16), 143 (100), 141 (7), 135 (8), 133 (7), 123 (8), 121 (14), 111 (52), 99 (20), 95 (23), 91 (9), 83 (19), 81 (25), 79 (28), 73 (16), 71 (24), 55 (48), 43 (60), 41 (38).

EXAMPLE 4

Preparation of
13-thia-13,14-dihydro-PGF$_{2\alpha}$-methylester-13-oxide and 15-epi-13-thia-13,14-dihydro-PGF$_{2\alpha}$-methylester-13-oxide 0.420 g (1.08 millimoles) of a 1:1 mixture of 13-thia-13,14-dihydro-PGF$_{2\alpha}$-methyl ester and 15-epi-13-thia-13,14-dihydro-PGF$_{2\alpha}$-methylester is dissolved in 5 ml of methanol and the solution is added to a 0.5 molar aqueous solution of 0.243 g (1.135 millimoles) of sodium periodate under stirring at 0° C. The reaction mixture is stirred at 0° C. for 3 hours, whereupon so much water is added that the precipitated crystalline sodium iodate goes into solution. The aqueous solution is extracted with 20 ml of dichloromethane. The extract is dried over magnesium sulfate, the solvent is distilled off and the residual oil is purified by column chromatography to separate the isomers (Kieselgel G; a 7:3 mixture of chloroform and acetone). Thus 0.152 g of 13-thia-13,14-dihydro-PGF$_{2\alpha}$-methylester-13-oxide and 0.139 g of 15-epi-13-thia-13,14-dihydro-PGF$_{2\alpha}$-methylester-13-oxide are obtained. Total yield 0.291 g (66.5%).

$R_F$=0.27 (Chloroform-acetone 7:3) $R_{F(15\text{-}epi)}$=0.22 (Chloroform-acetone (7:3).

Ms: M$^+$ 404 (7), m/e 389 (2), 387 (5), 373 (5), 333 (10), 285 (12), 284 (20), 242 (15), 241 (10), 224 (30), 222 (18), 210 (22), 204 (20), 185 (40), 173 (25), 163 (40), 147 (30), 86 (70), 45 (100).

Ms-15-epi: M$^+$ 404 (6), m/e 389 (2), 387 (6), 373 (4), 333 (10), 285 (12), 284 (16), 242 (16), 241 (10), 224 (30), 222 (16), 210 (22), 204 (20), 185 (40), 173 (23), 163 (36), 147 (34), 86 (62), 45 (100).

EXAMPLE 5

Preparation of the sodium salt of
13-thia-13,14-dihydro-PGI$_2$ 71 mg of (0.138 millimole) of 13-thia-13,14-dihydro-PGI$_2$-methyl ester are dissolved in 0.3 ml of methanol whereupon 2 ml of a 0.1 N sodium hydroxide solution is added and the reaction mixture is stirred at room temperature for 24 hours. After lyophilization of the solution 76 mg of the white compound named above are obtained.

What we claim is:

1. An optically active or racemic 13-thia-prostacycline of the Formula I

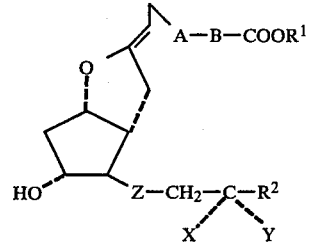

wherein
R$^1$ is hydrogen, a pharmaceutically acceptable cation or a straight or branched chain alkyl group having 1-5 carbon atoms;
R$^2$ is straight or branched chain alkyl having 4-9 carbon atoms or is phenoxymethyl substituted by a halo or a trifluoromethyl substituent: —A—B— is —CH$_2$—CH$_2$—, —CH=CH— of Z- or E-configuration or —C≡C—;
one of the symbols X and Y is hydrogen, methyl or ethyl and the other is hydroxy, tetrahydropyranyloxy, 1-ethoxy-ethoxy or trialkylsilyloxy; or
X and Y together form a —O—CH$_2$—CH$_2$—O— group; and Z is a sulfur atom or a —SO— group.

2. 13-thia-13,14-dihydro-PGI$_2$-methyl ester as defined in claim 1.

3. 15-epi-13-thia-13,14-dihydro-PGI$_2$-methyl ester as defined in claim 1.

4. 13-thia-13,14-dihydro-15-dehydro-PGI$_2$-methyl ester ethylene ketal as defined in claim 1.

5. Sodium salt of 13-thia-13,14-dihydro-PGI$_2$ as defined in claim 1.

6. A pharmaceutical composition having blood platelet aggregation inhibitory effect comprising as active ingredient a pharmaceutically effective amount of at least one compound in claim 1 in admixture with suitable inert non-toxic pharmaceutical carriers.

7. A method of treatment for blood platelet aggregation inhibiting effect which comprises administering to a susceptible subject an effective amount of a compound as defined in claim 1.

8. A compound of the formula II

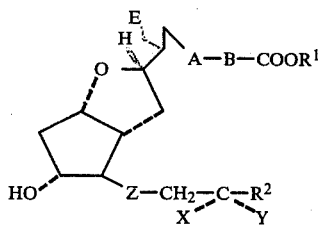

wherein $R^1$ is hydrogen, a pharmaceutically acceptable cation, or a straight or branched chain alkyl group having 1–5 carbon atoms;

$R^2$ is straight or branched chain alkyl having 4 to 9 carbon atoms or is phenoxymethyl substituted by a halo or a trifluoromethyl substituent;

—A—B— is —$CH_2$—$CH_2$—, —CH=CH— of Z- or E-configuration or —C≡C—;

one of the symbols X and Y is hydrogen, methyl or ethyl and the other is hydroxy, tetrahydropyranyloxy, 1-ethoxy-ethoxy, or trialkylsilyloxy; or X and Y together form a —O—$CH_2$—$CH_2$—O— group;

Z is a sulfur atom or a —SO— group, and E is halogen.

9. 5-iodo-13-thio-13, 14-dihydro-$PGI_1$, -methyl ester, as defined in claim 8.

10. 15-epi-5-iodo-13-thia-13,14-dihydro-$PGI_1$-methyl ester, as defined in claim 8.

11. 5-iodo-13-thia-13, 14-dihydro-15-dehydro-$PGI_1$-methyl ester ethylene ketal, as defined in claim 8.

* * * * *